United States Patent [19]

Hwang

[11] Patent Number: 4,824,718

[45] Date of Patent: Apr. 25, 1989

[54] POROUS FILM

[75] Inventor: Kirk K. Hwang, Woodbury, Minn.

[73] Assignee: Minnesota Mining and Manufacturing Company, St. Paul, Minn.

[21] Appl. No.: 128,793

[22] Filed: Dec. 4, 1987

[51] Int. Cl.$^4$ .................... B32B 3/10; B32B 7/02; B32B 7/04; B32B 33/00

[52] U.S. Cl. .................... 428/284; 428/286; 428/315.5; 428/315.9

[58] Field of Search .................... 428/284, 286, 315.5, 428/315.7, 315.9

[56] References Cited

U.S. PATENT DOCUMENTS

| | | | |
|---|---|---|---|
| 3,044,467 | 7/1962 | Campau | 128/290 |
| 3,214,501 | 10/1965 | Strauss | 264/49 |
| 3,426,754 | 2/1969 | Bierenbaum | 128/156 |
| 3,570,491 | 3/1971 | Sneider | 128/290 |
| 3,640,829 | 2/1972 | Elton | 161/159 |
| 3,643,154 | 2/1972 | Van Riemsdijk | 323/43.5 |
| 3,844,865 | 10/1974 | Elton et al. | 156/229 |
| 3,870,593 | 3/1975 | Elton et al. | 428/220 |
| 3,881,490 | 5/1975 | Whitehead et al. | 128/287 |
| 4,059,114 | 11/1977 | Richards | 128/287 |
| 4,194,041 | 3/1980 | Gore et al. | 428/422 |
| 4,341,216 | 7/1982 | Obenour | 128/287 |
| 4,539,256 | 9/1985 | Shipman | 428/315.5 |
| 4,609,584 | 9/1986 | Cutler et al. | 428/156 |
| 4,626,252 | 12/1986 | Nishizawa et al. | 604/370 |
| 4,699,733 | 10/1987 | Matsumura et al. | 282/521 |

*Primary Examiner*—William J. Van Balen
*Attorney, Agent, or Firm*—D. M. Sell; W. N. Kirn; C. Truesdale

[57] ABSTRACT

A disposable article such as a diaper or feminine hygiene product having a rattle-free, liquid impermeable, vapor permeable, microporous, polymeric film having pores defining passages extending therethrough, the passages being partially filled with a rattle-reducing additive material and a method for making same is disclosed.

11 Claims, No Drawings

4,824,718

POROUS FILM

FIELD OF THE INVENTION

The present invention relates to improved disposable articles such as diapers, adult incontinence products, disposable garments and feminine hygiene products. The products of this invention are characterize by the inclusion therein of a strong, liquid impermeable, vapor permeable polymeric matrix microporous film which significantly reduces the rattle, and enhances the hand of the article.

BACKGROUND OF THE INVENTION

Disposable articles such as diapers, adult incontinence products and feminine hygiene pads are generally constructed of three major components: a top sheet, an outer backsheet, and an intermediate liquid absorbent core. In normal use, the top sheet contacts a user's skin and provides channels to transport body fluids to the absorbent core which functions to retain the body fluids. In order to keep the fluids within the absorptive devices, typical backsheets are formed of leakproof materials. Recent diaper constructions incorporate elastic waist and leg strips to close the openings around the waist and the legs to prevent fluid leakage. Such designs, however, minimize air flow through the leg or waist openings and, since a typical backsheet is vapor impermeable, the interior of the diaper tends to become very damp and warm due to inadequate veniilation. This can result in diaper rash or other types of skin irritation. In addition, typical backsheets also rattle and crinkle, which can be of major concern to users of adult incontinence and feminine hygiene products. The noise produced is generally due to the stiffness of the backsheet. The other two components, the top sheet which is typically a soft perforated film or a light-weight nonwoven web (U.S. Pat. Nos. 3,044,467, 3,643,154) and the absorbent core which is mainly fluff pulp and tissue paper (U.S. Pat. No. 3,881,490) or high absorbency fibers (U.S. Pat. No. 3,570,491), do not contribute in any significant manner to the noise generated when the articles are twisted or rubbed.

Prior workers have attempted to produce rattle-free disposable products. U.S. Pat. No. 4,059,114 describes the use of a soft, rattle-free, vapor-permeable, body fluid impermeable web formed of blown microfibers in a feminine hygiene garment shield. A known disadvantage of blown microfiber material is that it can have an insufficient water holdout strength which results in liquid strike-through. The patent is also directed to the use of an additional moisture barrier formed of a butadiene-styrene copolymer, which is soft, rattle free, and high in water hold out but is not vapor permeable.

EPA No. 0,194,150 disclose the use of an elastomeric diaper backsheet formed of either ethylene-propylene-diene (EPDM) or ethylene propylene elastomer (EPM), mixed with ethylene-vinyl acetate copolymer (EVA) and an aromatic hydrocarbon oil. This approach provides low noise and good hand characteristics for diapers but offers no air permeability (breathability).

The art is replete with a wide variety of methods for producing porous films for disposable articles. U.S. Pat. No. 3,426,754 discloses a method for producing a microporous film for use as a leakproof backsheet for items such as diapers, sanitary napkins, and medical dressings. Microporosity is achieved by uniaxially cold stretching a polyolefin film until a void structure is formed by film failure, subsequently hot stretching the cold stretched film until the voids become open cells and finally heat setting the open structure. Controlled porosity is generally not attained and such a film tends to split when stretched in a direction transverse to that of the orientation.

U.S. Pat. No. 4,341,216 discloses a disposable diaper with a vapor permeable, relatively liquid impervious backsheet. The backsheets of the patent do not have the reduced rattle properties of films of the present invention.

Microporous sheet materials can also be made by incorporating a soluble filler in the sheet and then dissolving the filler to provide pores of various sizes within the material as described in U.S. Pat. Nos. 3,214,501 and 3,640,829. U.S. Pat. Nos. 3,844,865 and 3,870,593 disclose a process for making a porous structured polymeric film by dispersing particles which can be left in the film. Particles of inorganic salts such as calcium carbonate are blended into a polymer; a film is formed of the filled polymer and subsequently the film is stretched to provide porosity. The calcium carbonate fillers which remain in the final film serve as pore inducing agents when the film is stretched. While the porous films described, such as polypropylene, exhibit good strength, they have only limited moisture vapor transmission rates and the films are not rattle-free.

U.S. Pat. No. 4,626,252 describes a porous film for use as the leakproof sheet of a disposable diaper. The porous films are produced by blending a polyolefin resin with a filler and a liquid or waxy hydrocarbon polymer, forming the resulting resin composition into a film, and then stretching this film at least uniaxially by a factor of 1.2 or greater. The fillers act as pore inducers and the hydrocarbon polymer functions as both a processing agent and a plasticizer. As in U.S. Pat. Nos. 3,844,865 and 3,870,593, the porosity can be increased by increasing the amunt of filler in the film and by increasing the stretch ratio. However, when the amount of filler is increased to obtain higher porosity, the strength of the film decreases and there is a limit on the amount of stretch attainable. As a result, a limitation of this approach is its inability to obtain high permeability while maintaining satisfactory strength. In addition, pore uniformity depends on particle uniformity and dispersion in the film. The high percentage of filler and the absence of a rattle-reducing additive produces a film which does not have the rattle-free properties of the films of the present invention.

U.S. Pat. No. 4,699,733 describes a soft, vapor permeable film for use as the leakproof backsheet of a disposable diaper. The film is produced by blending a polyolefin resin and barium sulfate fillers, forming the molten resin composition into a film, and then stretching the film at least uniaxially by a factor of 1.5 to 7. The barium sulfate fillers act as the pore inducers at the time of stretching. This method has the same disadvantages as that associated with U.S. Pat. No 4,626,252. It does not achieve a good balance of permeability and strength.

U.S. Pat. No. 4,539,256 discloses another approach for making microporous films. A crystallizable thermoplastic polymer is melt blended with a compound in which the polymer will phase separate upon cooling below the crystallization temperature of the polymer. The mix is extruded in sheet form, followed by orientation in at least one direction, resulting in a microporous sheet with micropores distributed therethrough. The compound can then be removed from the microporous sheet by extraction, evaporation, leaching and the like to achieve high permeability.

U.S. Pat. No. 4,609,584 discloses an embossable porous film with satisfactory strength and high permeability for use as a diaper backsheet. At levels of high permeability, this film is also noisy which makes it less desirable for use in disposable products such as diapers and feminine hygiene products.

Copending U.S. application Ser. No. 940,731 discloses a method for making microporous films by incorporating a nucleating agent in a melt blend of a thermoplastic polymer and a compound miscible at the melting temperature of the polymer add which phase separates upon cooling at or below the crystallization temperature of the thermoplastic polymer. The incorporation of a nucleating agent makes the films stronger and more permeable than equivalent films without a nucleating agent.

SUMMARY OF THE INVENTION

The present invention relates to improved disposable articles such as diapers, adult incontinence products and feminine hygiene products. More specifically, this invention relates to such disposable articles having a strong, rattle-free, liquid impermeable but vapor-permeable microporous sheet material as a component thereof. The sheet materials used to make articles of the present invention are microporous polymeric matrix materials having pores partially filled with a rattle-reducing additive material capable of partially dissolving in the polymeric matrix. Preferably the pores define continuous passages extending through the polymeric matrix and opening into opposite surfaces thereof. The additive material is an ambient temperature liquid which comprises saturated aliphatic compounds with a varying range of molecular weights.

The present invention specifically relates to new and improved rattle-free disposable articles such as adult incontinence devices, sanitary napkins, single use garments, panty liners and diapers.

The present invention also relates to a process for making a rattle-free film for use in disposable articles.

DESCRIPTION OF THE INVENTION

The present invention relates to disposable articles such as diapers, adult incontinence products and feminine hygiene products including a liquid impermeable, vapor-permeable, rattle-free microporous sheet material as a component thereof.

In this invention, rattle-free means the associated rattle or noise produced by the article is below the background noise of a quiet office environment. In a normal office, the background noise generally ranges between 50 decibels (db) and 65 db. A quiet office environment generally ranges between 40 db and 55 db. A library environment usually has noise levels ranging between 30 and 40 db, and any noise below its background noise is undetectable. In this invention, an article is deemed to be rattle-free if its noise level, when twisted, is 40 db or below in a quiet environment (about 33 db).

The rattle-free properties of the disposable articles of the present invention are obtained by the inclusion of a rattle-reducing additive material in the microporous sheet material component. The additive material is in the form of a relatively viscous liquid or soft solid at ambient temperatures. The additive material is partially soluble in the polymeric matrix which results in the unique properties of the present invention. Surprisingly, when such additive materials are included, the sheet materials are more elastic than the starting sheet materials and have excellent moisture vapor transmission properties even though the rattle-reducing additive comprises from 5% up to 80% by weight of the sheet, with the rreferred range being 5% to 50%.

Suitable rattle-reducing additive materials are saturated compounds such as mineral oil, glycerin, petroleum jelly, low molecular weight polyethylene, polyethylene oxide, polypropylene oxide, polytetramethylene oxide, soft carbowax and the like and mixtrres thereof. Mineral oil is preferred because of its relatively low cost and excellent properties.

The polymeric matrix may be a crystallizable thermoplastic polymer of a polyolefinic nature such as high density polyethylene, linear low density polyethylene, polypropylene, polybutylene, poly-4-ethyl pentene, a block copolymer or copolymers of ethylene and propylene, or other modified polyolefins. These resins can be used either singularly or in a mixture. It is preferred to use polypropylene, either in its pure form or a modified polypropylene, with a molecular weight in the range of 50,000 to 500,000 with a melt flow index ranging from 0.1 to 8. If the molecular weight is lower than 50,000, the film will have poor stretchability resulting in orientation problems and a resulting poor vapor permeability. It is advantageous to use modified polypropylenes with a high melt strength for high speed film production.

The preferred rattle-reducing additive comprises an ambient temperature liquid saturated aliphatic compound which acts both as a pore forming and rattle-reducing additive. It is desirable to have part of the aliphatic compound dissolved in the polymeric matrix to plasticize the polymer and give the resulting films good hand and reduced rattle characteristics. It is desirable that the aliphatic compound "match" the thermoplastic polymer used in the resin so that the two components are miscible in the molten state but partly phase separate when cooled to below the crystallization temperature of the thermoplastic polymer. In the present invention, it is preferred to select a resin comprising polypropylene and a hydrocarbon such as mineral oil. The oil has a preferred viscosity range of 100 to 1,000,000 centipoise with boiling point about 300° C. If the viscosity is too high, the result is low permeability of the films produced. If the viscosity is too low, the hydrocarbon tends to bloom to the surface thereby causing the film to have a tacky feel.

A particular combination of polymer matrix and rattle-reducing additive may include more than one polymer, and more than one additive compound. Optionally, the composition may have blended therein certain adjunctive ingredients. These ingredients should be limited in quantity so as not to interfere with the formation of the microporous material and so as not to result in unwanted exuding of the adjunctive ingredient. Such ingredients may include antistatic materials, dyes, pigments such as titanium dioxide, plasticizers, toughening agents, flame retardants, antioxidants, UV absorbers, and the like. When used, the amount of such adjunctive ingredients is typically less than about 10% of the weight of the polymer component, and preferably less than about 2% by weight.

The use of a nucleating agent system is critical to achieving a satisfactory overall balance of film properties. It has been found that just one inorganic nucleating agent such as talc is used, the film exhibits satisfactory permeability but the tensile strength of the fil may be inadequate for processing and/or final product use. If only an organic nucleating agent is used, the materials are strong but the materials may be less than the optimum for use in certain disposable products due to a high coefficient of friction and low permeability.

The preferred nucleating system of the present invention consists of two agents. The primary agent is a solid organic compound such as an organic acid which can dissolve in the thermoplastic polymer in a molten state at a temperature at least 10° C. above the crystallization temperature of the thermoplastic polymer. When the thermoplastic resin is cooled to a point approaching the crystallization point of the polymer, the organic nucleating agent phase separates and facilitates crystallization of the thermoplastic polymer which subsequently phase separates from the aliphatic compound. If the nucleating agent phase separates and crystallizes too late (which would occur at a temperature too close to the crystallization temperature of the thermoplastic), the structure of the film will not be as fine and the film will have reduced stretchability and limited permeability levels. In this invention, suitable primary nucleating agents, which are added in small amounts, generally 0.05 to 5% by weight, preferably from 0.1 to 2% and most preferably from 0.1 to 1.2%, include solid organic acids such as mono- or polyacids, e.g., carboxylic acids, sulfonic acids, and phosphonic acids, and solid organic alcohols such as dibenzylidene sorbitol.

The secondary nucleating agent of the system is an inoraanic material which, when used with the primary nucleating agent, provides a surprising effect in achieving a balance of low surface friction, strength and permeability. The inorganic nucleating agent can be selected from talc, titanium dioxide, calcium carbonate, magnesium carbonate, barium carbonate, magnesium sulfate, barium sulfate, and the like. The particles are often disk-shaped with a thickness in the range of 0.2 to 0.5 microns and diameters ranging from 0.2 to 110 microns, with the majority of diameters in the range of 0.2 to 5 microns. In this invention, only very small amounts of the inorganic nucleating agent are used, generally from 0.05 to 5% by weight, preferably from 0.1 to 2% and most preferably from 0.1 to 1.2%, and fine particles are preferred. At 5 parts by weight or more, the film tends to be weak.

Preferred combinations of organic and inorganic nucleating agents are adipic acid and talc, adipic acid and titanium oxide, adipic acid and calcium carbonate, adipic acid and magnesium sulfate, succinic acid and talc, succinic acid and titanium dioxide, succinic acid and calcium carbonate, succinic acid and magnesium sulfate. The most preferred nucleating agent systems for polypropylene are a combination of adipic acid and talc or succinic acid and talc.

Based on 100 parts by weight of thermoplastic, it is preferred that the rattle-rdducing additive compound is mixed in the crystallizable thermoplastic in an amount between 25 to 45 percent by weight. Both the primary and secondary nucleating agents are then added in a preferred range of 0.1 to 1.2 parts by weight. An increase in the overall percentage of rattle-reducing compound results in a more permeable film with the same orientation. If the percentage falls below 20 percent by weight, the resulting film has poor permeability. If the percentage exceeds 60 percent by weight, the film will be too weak and impractical for processing and subsequent use in disposable articles.

When the rattle-reducing additive is preblended with the thermoplastic and thermally formed into a film, stretching is required to generate the final film porosity. It is preferred that heat setting is performed during or just after the stretching to stabilize the film microstructure. Biaxial orientation gives a more balanced strength in all directions across the film than uniaxial orientation. Uniaxial orientation is generally done in the machine direction (the direction the film is extruded). The recommended stretching ratio in one direction is in the range of 1.5 to 3. If the stretch ratio is lower than 1.5, the pore size may not be large enough to provide good permeability. On the other hand, if the film is over-stretched, permeability can be impaired due to collapsing of the pores. The stretch limit is dependent on the formulation.

The sheets or films of the invention are oriented by stretching them uniaxially or biaxially at a temperature between 10° C. (50° F.) and 10° C. below the melting temperature of the polymeric matrix material.

The porosity of the porous film is determined by the amount of saturated aliphatic compound used, the stretch ratio, as well as the type and amount of nucleating agents utilized. The pore size of the films is in the range of 0.1 to 100 microns. A majority of the pores is in the range of 0.2 to 5 microns.

If it is desired to reduce the level of rattlereducing additive in a film, the additive can be removed by partial leaching with a suitable solvent. If it is desired to increase the level of additive, the additive can be added by any convenient process such as misting, brushing, immersion, soaking and the like. If it is desired to reduce the rattle in other known porous films, it is possible to use these same processes. It has been found that by heat setting films to which rattle-reducing compounds have been added (at moderate temperatures of 40 to 100° C. for a short time such as one to five minutes), the additive is distributed sufficiently uniformly such that the resulting films have a reduced coefficient of friction, high moisture vapor transmission and low rattle properties.

The reduced coefficient of friction of the films used in the articles of the present invention is a significant advantage during processing. For example, it permits more rapid and efficient processing on belts when making diaper backsheets.

Overall, the thickness of the sheet materials used in the articles of the present invention is in the range of 5 to 250 microns. The film can also be surface treated by processes such a embossing, fiber coating, corona discharge, chemical modification, and the like.

The sheet materials used in the articles of the invention may be embossed according to the method of U.S. Pat. No. 4,609,584, the disclosure of which is incorporated herein by reference. The embossing can cover up to 50% of the surface area of the films. Two or more layers of the sheet materials may be used in disposable articles of this invention.

In the Examples, the values reported as Gurley numbers were measured by a "Permeability Test" which is described below. Properties such as moisture vapor transmission (MVT), tensile strength and elongation were measured by methods described below. The bubble point was measured according to ASTM F-316-80 and represents the largest effective pore size measured in microns. The water holdout was measured according to ASTM D-751-79 and the coefficient of friction (COF) was measured against the film itself using ASTM D-1894. The sliding speed is 6 inches per minute. The flexibility was measured using a test described below and tear strength was measured pursuant to ASTM D-1922 (pendulum method). In order to measure the sound generaed by the films of the invention, a sound-flex test method and machine described below was used.

Sound-Flex Test Method

A sound analysis tsst was used to measure the degree of rattle of the films and articles of this invention. Briefly, two clamps are separately sequentially driven in a clockwise and counterclockwise fashion. The distance between the clamps is varied depending on the size of the sample tested. A sample is placed in the clamps and the clamps are rotated to distort the sample. As the sample is distorted, an associated rattle of the sample is given off and this rattle is received by a sensor as a signal. The signal is quantified into both a decibel reading and a frequency response. In order to insure consistent and accurate results, the test is performed in an anechoic chamber with controlled background noise. The anechoic chamber dampens echoes and background noise. A 43 db background is used to simulate a quiet office environment. A background of 33 db is used to simulate a library environment.

Permeability Test

The test for air permeability was ASTM D-72658 which test employs a "Gurley" densimeter manufactured by W. and L. E. Gurley and Sons. Results are reported as a "Gurley" number which is the time in seconds for 50 ml of air to pass though one square inch (6.45 cm$^2$) of the sample under a pressure of 4.9 inches (124 mm) of water. Useful microporous films have been found to have a Gurley number of 5 to 1400 sec/50 ml, preferably 5 to 1000, and most preferably less than 500 sec/50 ml.

Moisture Vapor Transmission Test

The method for determining moisture vapor transmission employs an apparatus described in ASTM E96-B66B, modified as disclosed in U.S. Pat. No. 4,194,041. The test is conducted by filling a cup with 80 cc of water, sealing the sample being tested to the lip of the cup with silicone adhesive, weighing the cup and its contents including the attached sample to the nearest 1/100 gram and placing the cup in a rubber collar under tension beneath the lip at the mouth of the cup. The assembly is then suspended upside-down through a circular opening in a support plate in an environmental chamber so that the sample is disposed 10 cm above the bottom surface of the chamber. The chamber is held at a temperature of about 23° C. (73° F.) and a relative humidity of 50±2 percent and a linear air flow of 250 cm/sec is directed through the air space between the bottom of the chamber and across the surface of the sample being tested. The sample is permitted to remain in this position for a 15 hour period, removed and re-weighed to an accuracy of 1/100 of a gram. The moisture vapor transmission rate is then reported in g/m$^2$ for a 24 hour period.

The sheet materials used in the articles of the present invention have a moisture vapor transmission rate of at least 1000 g/m$^2$/day at 23° C. and 50% relative humidity.

Tensile Strength and Elongation

The tensile strength of the samples was measured according to ASTM D-882 using a die-cut rectangular test specimen which was 10.16 cm (4.0 inches) long by 2.54 cm (1 inch) wide except for the ends which were wider for grasping in the jaws of an "Instron" tensile strength testing device Model U-22. The jaws were set 5.08 cm (2.0 inch) apart and operated at a crosshead speed of 25.4 cm/min (10 inches/min) until the maximum tensile strength was reached just before breaking. The maximum tensile strength at break and the amount of stretch or elongation in centimeters at break were measured. Samples were tested "ambient", i.e., equilibrated under ambient temperature (about 23° C.) and humidity (about 50% relative humidity) conditions.

Flexibility Test

The film specimen to be tested is placed over a measured slot opening extending across the platform of the instrument. TThe instrument is a Thwing-Albert Handle-O-Meter. The slot opening is adjusted to 20 mm or 6 mm depending on the characteristics of the material being tested. The penetrator arm is pivoted to ride on an eccentric cam engaging the specimen and forcing it into the slot. Flexibility and surface friction of the specimen are the factors which affect the movement of the penetrator arm into the slot.

Stiff material will resist the motion of the penetrator arm more than soft material, and rough material will resist being dragged over the edge of the slot more than smooth material. A linear variable differential transformer detects the sum of the two resistances and registers the combined values on a calibrated digital voltmeter. Samples were tested at a 20 mm slot opening.

The following Examples are provided to more specifically illustrate the invention.

EXAMPLE 1

Microporous sheet materials of melt blends of crystallizable polypropylene with a melt flow index of 0.8 (available under the trade designation Profax 6723 from Hercules), mineral oil (available under the trade description Nujol from Plough, Inc.) were prepared following the general procedure described in U.S. Pat. No. 4,539,256 wth the addition of nucleating agents. The melt blend of the components was extruded upward through a 5.08 cm diameter annular die at a 1.4 m/minute take-off speed. The annular die was maintained at 221° C. during the extrusion. The tubular-shaped extrudate was cooled by blowing air against the outside surface of the tube. The tube was expanded into a bubble 25 cm in diameter by air pressure. The finished film was subsequently elongated in the length direction by 150% at 65.6° C.

It will be seen that the nucleating agents utilized affect microporous film properties differently. Combinations of different nucleating agents produces superior films for disposable products such as diaper baksheets. The films listed in Table 1 were prepared following the process described except Group E which used a different polypropylene (Profax 6823) with a melt index of 0.3.

Group A includes films employing as nucleating agents a mixture of adipic acid (AA) and talc (T).

Group B includes films employing adipic acid a the nucleating agent.

Group C is a film employing talc as the nucleating agent.

Group D employs an equal mixture of adipic acid and talc with Irganox B225 added as an antioxidant.

Group E employs a 1:3 ratio of adipic acid and talc with Irganox B225 added as an antioxidant.

Films of groups A, B,DD and E, in which adipic acid was used, were stretched by 225% and could be stretched over 300% without breaking. The film listed in Group C which used talc as the sole nucleating agent was stretched to 150% and tended to break at about 190% elongation.

Table 1 shows that films nucleated with adipic acid (Group B) were stronger and tougher but had lower MVT values than the film nucleated with talc (Group C). However, films in Group A and E which used a mixture of adipic acid (AA) and talc (T) as the nucleating agent had the combination of advantages of both Groups B and C, and were better candidates for diaper backsheet applications. The major advantages of films using both nucleating agents are: high MVT, toughness, low surface friction, and good hand.

cinicaacid is used as the organic nucleating agent for film I and adipic acid is used for film J. Similar properties are found in these two films.

TABLE 2

| FILM GROUP | PP/OIL/AA/ T/Irganox B225* | ORIENTA- TION % | GURLEY (sec/50 cc) | MVT (g/m²/day) | TENSILE (kg/cm²) MD | TENSILE (kg/cm²) TD | ELONGATION (%) MD | ELONGATION (%) TD | COEF- FICIENT OF FRICTION | NOISE (db) |
|---|---|---|---|---|---|---|---|---|---|---|
| D | 57.6/42/.12/.12/.12 | 225 | 36 | 11700 | 161 | 77 | 51 | 170 | 0.4 | 36 |
| E | 59.4/40/.12/.36/.12 | 225 | 124 | 4500 | 197 | 104 | 92 | 196 | 0.29 | 40 |
| F | 57.2/42/.11/.57/.11 | 225 | 31 | 11546 | 150 | 71 | 59 | 119 | 0.3 | 37 |
| G | 61.6/38/.12/.12/.12 | 225 | 295 | 5100 | 236 | 86 | 67 | 231 | 0.3 | 37 |
| H | 61.1/38/.12/.6/.12 | 225 | 98 | 6700 | 210 | 90 | 79 | 212 | 0.3 | 38 |
| I | 59.4/40/.12/.36/.12 | 225 | 65 | 6800 | 189 | 90 | 114 | 202 | 0.3 | 39 |
| J | 59.4/40/.12/.36/.12 | 225 | 81 | 8000 | 200 | 86 | 117 | 198 | 0.3 | 36 |

*percent of total composition, by weight
Background noise: 33 db

EXAMPLE 3

A sanitary napkin was constucted using a tubular design. A fluff pulp core of 2.9 g of Foley Fluffs ® (available from Buckeye Cellulose Corp., Memphis, Tenn.) was enclosed in tissue paper provided with the Fluffs and then enclosed in a sheet of a standard carded nonwoven biconstituent web of high density polyethylene and polyethylene terephthalate (50:50) of basis weight 20g/m² to form a pad about 0.75 inches (1.9 cm) tick, 2.75 inches (7.0 cm) wide and 6.5 inches (16.5 cm) long. The long edge of the nonwoven sheet was folded over and the short edges were adhered with an adhesive transfer tape (3M brand transfer tape No. 1524 available from 3M Co., St. Paul, MN). A rattle-free porous film prepared as described hereinabove (Example 1, Table 1, Group D) was cut to fit over one side of the pad and adhered to the edges by the use of the above adhesive.

An analogous pad was constructed by substituting a

TABLE 1

| FILM GROUP | PP/OIL/AA/ T/Irganox B225* | ORIENTA- TION % | GURLEY (sec/50 cc) | MVT (g/m²/day) | TENSILE (kg/cm²) MD | TENSILE (kg/cm²) TD | ELONGATION (%) MD | ELONGATION (%) TD | COEFFI- CIENT OF FRICTION | NOISE (db) |
|---|---|---|---|---|---|---|---|---|---|---|
| A | 57.8/42/0.1/0.1 | 225 | 66 | 8091 | 155 | 61 | 99 | 213 | .37 | 45 |
|  | 61.8/38/0.1/0.1 | 225 | 178 | 6455 | 205 | 85 | 123 | 276 | .35 | 49 |
|  | 59.2/40/0.4/0.4 | 225 | 59 | 8000 | 173 | 49 | 47 | 157 | .39 | 48 |
|  | 57.3/42/0.1/0.6 | 225 | 77 | 7432 | 165 | 72 | 142 | 249 | .50 | 48 |
| B | 59.94/40/0.06/0 | 225 | 380 | 2864 | 220 | 92 | 165 | 204 | .97 | 48 |
|  | 59.88/40/0.12/0 | 225 | 2061 | 3068 | 217 | 133 | 250 | 490 | .9 | 48 |
| C | 60.4/39/0/0.6 | 150 | 17 | 6273 | 84 | 49 | 17 | 24 | .24 | 49 |
| D | 57.6/42/0.12/0.12/0.12 | 225 | 36 | 11700 | 161 | 77 | 51 | 170 | 0.40 | 44 |
| E | 59.4/40/0.12/0.36/0.12 | 225 | 124 | 4500 | 197 | 104 | 92 | 196 | 0.29 | 44 |

*percent of total composition, by weight
Background noise: 43 db

EXAMPLE 2

Noise levels ff the films are measured against a background noise of 43 db. Normally, the noise level in a quiet office environment is about 40 to 55 db. When the film's crinkling is less than the background noise, the film's noise becomes undetectable. As shown in Table 1, films D and E have a negligible contribution to the total noise level of 44 db when measured against a background noise level of 43 db. Therefore, a background noise of 33 db, simulating a quiet environment such as a library, is reported in Table 2 including films D and E from Table 1.

Films in this example were made according to the process described in Example 1. Samples D, E, F, G, and H show a percentage of talc ranging from 0.2% to 1% in combination with 0.2% of adipic acid. Films I and J have the same composition ratio, except sucstandard diaper coverstock, 1.25 mil (0.032 mm) white polyethylene film containing titanium dioxide, EPC-00772 (available from Edison Corp., South Plainfield, N.J.) for the rattle-free porous film.

The pads were compared using the sound flex test described above. Pads were placed in the apparatus by fitting them around cylindrical drums and taping, and rotating the pads back and forth about a 45° axis. The napkin of the present invention had a noise level of 45 db and the napkin with the standard diaper coverstock had a noise level of 55 db. The background noise level was 43 db.

EXAMPLE 4

A diaper was prepared using a rectangular design. A fluff pulp core of 30 g of Foley Fluffs enclosed in tissue paper as in Example 3 was enclosed between one diaper size sheet of the carded nonwoven web used in Example 3 and one sheet of rattle-free porous film prepared as described hereinabove (Example 1, Table 1, group E) and the sheets were adhered at the edges by An analogous diaper was constructed replacing the rattle-free porous film sheet with a sheet of standard coverstock white polyethylene film EPC-00772.

The diapers were compared using the sound flex test described above. Diapers were placed in the apparatus by fitting them in a roll conformation around cylindrical drums. They were fastened with 0.75 inch (1.9 cm) width adhesive tape and rotated back and forth about a 45° axis. The diaper of the present invention had a noise level of 49 db and the diaper made using standard materials had a noise level of 59 db. The background noise level was 43 db.

EXAMPLE 5

Two diapers were prepared according to Example 4 except elastic leg bands were provided on each of tee diapers by adhering elastic strips (Scotch brand elastic KER-2210) to the inside of the nonwoven sheet before sealing the fluff inside.

The noise level of the diaper of the invention was 49 db and the noise level of the conventional diaper was 60 db. The background noise level was 43 db.

EXAMPLE 6

Absorbent napkins (8 in × 4 in) were prepared according to Example 3 using 5.0 g of sorbent core and the nonwoven sheet of Example 3 was replaced by nonpermeable 2 mil (0.051 mm) polyethylene film. The nonpermeability of the film had been prechecked by both an MVT test and a Gurley porosity test and showed no water vapor transmission over a 24 hour period. The films of the napkin were heat sealed on all edges.

Into the sorbent core of these napkins was injected 60 ml of water at about 37° C. using a large needle syringe. The needle hole was sealed using a small piece of nonpermeable tape. The weight loss of the napkins was measured by placing them on a balance with the porous film facing up in ambient conditions at about 75° F. (24° C.), 30% relative humidity and weighing them at ten minute intervals for 6 hours. At the end of 6 hours the napkin of the invention had lost 12.4 g and the nonpermeable film napkin had lost 2.0 g, demonstrating that the rattle-free film had excellent moisture vapor transmission.

What is claimed is:

1. A disposable article comprising a top sheet, an intermediate liquid absorbent core and an outer backsheet, said backsheet being a rattle-free, liquid impermeable, vapor permeable, microporous film with a rattle-reducing additive material partially filling said micropores uniformly distributed through said film, said film having a moisture vapor transmission rate of at least 2000 grams per square meter per 24 hours at 23° C. and 50% relative humidity.

2. The disposable article of claim 1 wherein said film has an air permeability Gurley number less than 500 seconds per 50 cc.

3. The disposable article of claim 2 wherein the film has a thickness ranging from 5 to 250 micrometers.

4. A method of making the microporous film of the disposable article of claim 1, comprising the steps of:
   (a) forming a blend of a crystallizable thermoplastic polymer, rattle-reducing additive material and nucleating agent system;
   (b) extruding the blend into a film; and
   (c) orienting said film by stretching at a temperature in the range of 10° C. to 10° C. below the melting temperature of said thermoplastic polymer.

5. A method according to claim 4 wherein the rattle-reducing additive material is selected from mineral oil, glycerin, petroleum jelly, soft carbowax, low molecular weight polyethylene, polyethylene oxide, polypropylene oxide, polytetramethylene oxide or mixtures thereof.

6. A method according to claim 4 wherein the crystallizable thermoplastic polymer is selected from polypropylene, polyethylene and polyethylene-polypropylene.

7. A method according to claim 4 wherein the rattle-reducing additive material comprises 5 to 50% by weight of the microporous film.

8. A method according to claim 4 wherein the nucleating agent system comprises a solid organic acid and an inorganic compound.

9. A method according to claim 8 wherein the solid organic acid is adipic acid and the inorganic compound is talc.

10. The disposable article of claim 1 wherein up to 50% of the surface area of said microporous film has been embossed.

11. A microporous film made according to the process of claim 4.

* * * * *

UNITED STATES PATENT AND TRADEMARK OFFICE
CERTIFICATE OF CORRECTION

PATENT NO. : 4,824,718
DATED : APRIL 25, 1989
INVENTOR(S) : KIRK W. HWANG

It is certified that error appears in the above-identified patent and that said Letters Patent is hereby corrected as shown below:

Col. 1, line 30, "veniilation" should be --ventilation--.
Col. 1, line 55, "disclose" should be --discloses--.
Col. 3, line 14, "add" should be --and--.
Col. 4, line 8, "rreferred" should be --preferred--.
Col. 5, line 3, "fil" should be --film--.
Col. 5, line 33, "inoraanic" should be --inorganic--.
Col. 5, line 59, "-rdducing" should be -- -reducing --.
Col. 7, line 6, "generaed" should be --generated--.
Col. 7, line 11, "tsst" should be --test--.
Col. 8, line 22, "TThe" should be --The--.
Col. 8, line 60, "baksheets" should be --backsheets--.
Col. 8, line 67, "a" should be --as--.
Col. 9, line 20, "DD" should be --D--.
Col. 9, line 3, "ff" should be --of--.

UNITED STATES PATENT AND TRADEMARK OFFICE
CERTIFICATE OF CORRECTION

PATENT NO. : 4,824,718

DATED : APRIL 25, 1989

INVENTOR(S) : KIRK W. HWANG

It is certified that error appears in the above-identified patent and that said Letters Patent is hereby corrected as shown below:

Col. 10, line 1, "cinicaacid" should read --cinic acid --.

Col. 10, line 27, "tick" should be --thick--.

Col. 11, line 3, insert "adhesive." after --edges by--.

Col. 11, line 19, "tee" should be --the--.

Signed and Sealed this

Nineteenth Day of December, 1989

Attest:

JEFFREY M. SAMUELS

Attesting Officer     Acting Commissioner of Patents and Trademarks